United States Patent [19]

Kanshin et al.

[11] 4,397,311

[45] Aug. 9, 1983

[54] SURGICAL INSTRUMENT FOR STAPLE SUTURING OF HOLLOW ORGANS

[75] Inventors: Nikolai N. Kanshin; Vladimir M. Fedotov; Boris A. Smirnov; Igor A. Guskov, all of Moscow, U.S.S.R.

[73] Assignee: Vesesojuzny Nauchnoissledovatelsky I Ispytatelny Institut, U.S.S.R.

[21] Appl. No.: 203,345

[22] Filed: Nov. 3, 1980

[30] Foreign Application Priority Data

Dec. 20, 1979 [SU] U.S.S.R. .............................. 2856033

[51] Int. Cl.³ ............................................. A61B 17/04
[52] U.S. Cl. ................................ 128/305; 128/334 R; 227/DIG. 1
[58] Field of Search ............. 128/334 R, 305; 227/19, 227/DIG. 1

[56] References Cited

U.S. PATENT DOCUMENTS

| 3,079,606 | 3/1963 | Bobrov et al. | 227/DIG. 1 X |
| 3,606,888 | 9/1971 | Wilkinson | 128/334 R |
| 4,120,302 | 10/1978 | Ziegler | 128/322 |

FOREIGN PATENT DOCUMENTS 571254 10/1977 U.S.S.R. .......................... 128/334 R

OTHER PUBLICATIONS

Records of Pathology, vol. XL, Issue 8, pp. 56–61, *Sutureless Anastomoses in Surgery* by Kanshin et al. Proceedings of the USSR Acadamy of Sciences, Biological Series, 1979, No. 1, pp. 13–17.

*Primary Examiner*—Michael H. Thaler
*Attorney, Agent, or Firm*—Steinberg & Raskin

[57] ABSTRACT

Described herein is an instrument, comprising a staple body and a supporting body hingedly connected thereto, both having longitudinal jaws. The staple body has staple magazines and a staple ejector. The supporting body has a die for bending the staples when suturing. A recess is provided at the base of one of the jaws on the side facing the hinge joint interconnecting the instrument bodies, the recess defining a free space between the jaws when they are brought together. The jaws are adapted to have springy elastic spacers mounted and held thereon with a possibility of subsequent releasing therefrom, said spacers being arranged on the side facing the inner compressing surfaces of the jaws so as to be stitched up together with the organs being sutured.

The instrument disclosed in the present invention is successfully applied for establishing lateral anastomoses and interintestinal compression anastomoses, as well as for stitching up the mesentery.

3 Claims, 6 Drawing Figures

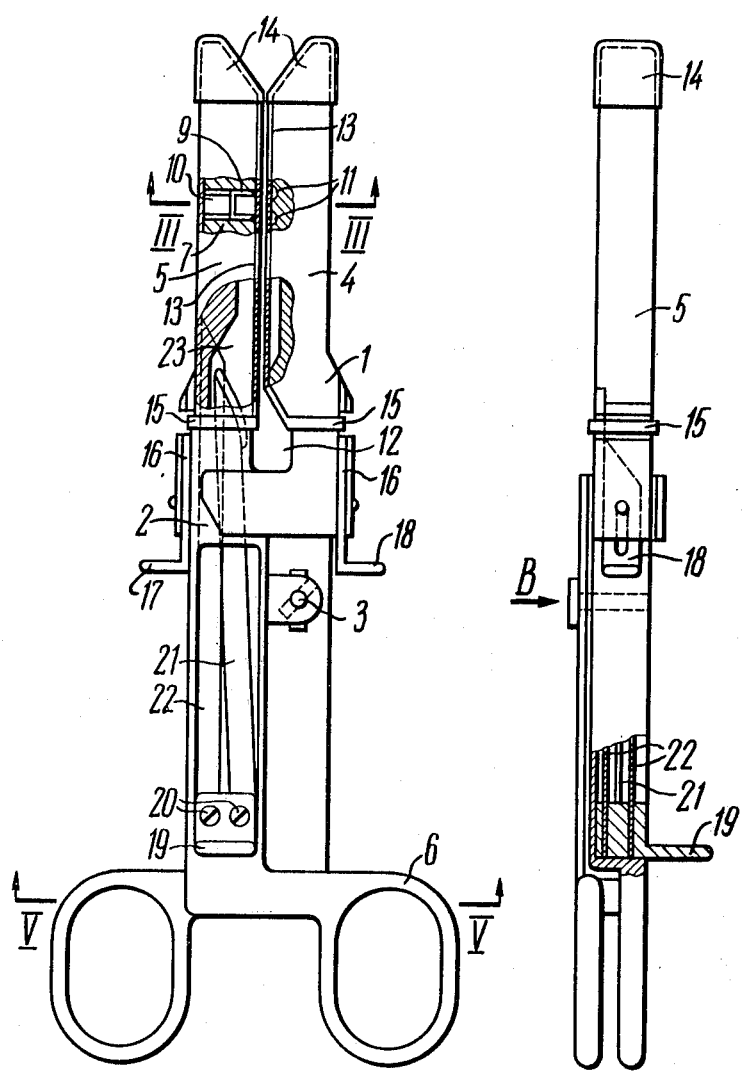

SURGICAL INSTRUMENT FOR STAPLE SUTURING OF HOLLOW ORGANS

TECHNICAL FIELD

The present invention relates to medical equipment and has particular reference to a surgical instrument for staple suturing of hollow organs, e.g., for establishing lateral gastrointestinal and interintestinal anastomoses to provide a decompression in the suture applied, whereby the suture elements are rejected over a period of time and are removed naturally, as well as to stitching up considerable lengths of the mesentery.

BACKGROUND OF THE INVENTION

Known in the art are a number of various devices for establishing compression anastomoses of hollow organs of the gastrointestinal tract by compressing the tissues in the anastomotic zone with such a force that results in rejecting the devices over a period of time and their natural removal (cf., e.g., "Sutureless anastomoses in surgery of the gastrointestinal tract with and without permanent magnetic field" by N. N. Kanshin et al. Records of pathology, 1978, v. XL, issue 8, pp. 56∝61 (In Russian); "On some regularities governing the tissue compression and regeneration processes involved in establishing sutureless anastomoses of hollow organs of the gastrointestinal tract" by L. A. Piruzian et al. Proceedings of the USSR Academy of Sciences, Biological series, 1979, No. 1 pp. 13–17 (in Russian)). These devices are made of two flat plates of a magnetic material, which attract each other, or two flat rings likewise attracting each other. However, the abovesaid devices made as magnetic plates fail to provide primary patency of the alimentary tract, while the magnetic rings are unsuitable for the purpose as practical experience has demonstrated, due to high stiffness and large weight.

One more suturing instrument disclosed in USSR Inventor's Certificate No. 571,254 is known to comprise a tubular body, a staple head linked thereto and provided with staple slots, a circulary knife, a detachable thrust head with depressions and a movable screw locking the head in position, soft elastic spacers shaped as circular troughs and located on the suturing surfaces of the staple and thrust heads.

The abovesaid instrument is capable of establishing compression anastomoses on the organs of the digestive tract using end-to-end or end-to-side technique alone. The instrument is unsuitable for establishing latera gastrointestinal and interintestinal compression anastomoses, which are frequently encountered in modern surgical practice.

An instrument protected by U.S. Pat. No. 3,079,606 is known for establishing lateral gastrointestinal and interintestinal anastomoses by the side-to-side technique.

The instrument is known to comprise hinge-joined supporting and staple bodies having longitudinal jaws, the former body carrying a staple magazine and an ejector to feed the staples from the magazine for suturing, and a knife for making a longitudinal incision along the length of the applied sutures applied, while the latter body has a die for bending the staples in the course of suturing. However, this instrument suffers from a number of disadvantages, stemming largely from its being not adapted for establishing lateral compression anastomoses.

The afore-mentioned instrument allows springy elastic spacers to be mounted on its jaws. However establishing a lateral compression anastomosis requires incisions or punctures for the jaws to pass through, which are then to be stitched up manually. This deleteriously the quality of the compression anastomosis thus established. Though the zone of the compression suture features good biological tightness and provides for good asepsis in the course of tissue healing, the adjacent zone of manual suture, even when possessing high mechanical strength, suffers from disturbed biological tightness thereof, whereby inflammatory and adhesion-forming process are liable to develop. As a result, the potency of the established anastomosis is reduced on which account cicatricial tissue are later liable to form in the anastomotic zone.

Moreover, in order to withdraw the instrument jaws from the interior of the hollow organs involved after their walls have been sutured with staples together with the elastic spacers, the latter must be separated from the jaws, which provide to be difficult with a given construction of the instrument. Thus, one has to enlarge the punctures made in the wall of the organs being anastomosed, in order to intersect the straps holding the spacers to the instrument jaws. This of course impairs the quality of the compression anastomosis established.

Apart from a quality formation of anastomoses on the organs of the gastrointestinal tract, one more important task of a surginal intervention in these organs is to stitch up the mesentery, which needs establishing of any anastomosis. Besides, stitching up the mesentery following the excision of morbidly changed intestines involves considerable lengths of the gastrointestinal tract, which may amount to a few scores of centimeters.

Such a case requires, apart from reliable constriction of different-size blood vessels running through the mesentery, also application of longer sutures, i.e., needs higher productivity of the suturing instrument. This makes it possible to cut down the operating time several fold.

The known instrument as per U.S. Pat. No. 3,079,606 when applied for stitching up the mesentery with the use of elastic spacers, requires some additional manipulations with the cutting instruments in order to separate the spacers from the instrument jaw, and turns of the suturing instrument for the spacers to take out of the bottom jaw, which is far from being practicable at every time, e.g., deeply in the operative wound and affects adversely the productivity of the instrument.

OBJECTS OF THE INVENTION

It is an essential object of the present invention to provide an instrument for suturing hollow organs, capable of establishing lateral gastrointestinal and interintestinal compression anastomoses featuring a separated zone of manually applied suture, and of accelerating the operations of stitching up the mesentery to attain a reliable hemostasis.

It is another object of the present invention to provide an instrument for suturing hollow organs, capable of attaining higher quality and reliability of the lateral compression anastomoses.

Among other objects of the present invention one is to reduce the amount of trauma inflicted upon the tissues of the organs being sutured and provide favourable reunion of the tissues involved within the postoperative period.

BRIEF DESCRIPTION OF THE INVENTION

The aforesaid and other objects are accomplished by providing a surgical instrument for suturing hollow organs by means of staples, especially when establishing lateral anastomoses and stitching up the mesentery by means of staples, comprising supporting and staple bodies hinge-joined to each other, both provided with longitudinal jaws the staple body has a staple magazine and an ejector to feed staples out of the magazine for suturing, while the supporting body has a die for bending the staples in the course of suturing. According to the present invention, a recess is formed at the base or bottom of at least one of the jaws on its side proximate the hinge joint interconnecting the bodies, said recess defining a free space between the jaws when brought together, while both of the jaws are adapted for mounting springy elastic spacers thereon and held thereto with a possibility of subsequent releasing, said spacers being arranged on the side facing the inner compressing surfaces of the jaws so as to be stitched up together with the organs being sutured.

Provision of the abovesaid recess at the base or bottom region proximate to the hinge joint of one of the jaws with the possibility of mounting and holding springy elastic spacers on to the jaws (with subsequent releasing of said spacers therfrom) on the side facing the inner compressing surfaces of the jaws renders it possible to establish lateral gastrointestinal and interintestinal anastomoses featuring an isolated zone of manually applied suture, and to accelerate the mesentery stitching-up operation to give a reliable hemostasis. This is turn adds to the quality and reliability of the lateral compressionn anastomoses, significantly reduces the amount of trauma inflicted upon the tissues of the organs operated upon during suturing and facilities a subsequent favourable reunion of the tissues within the postoperative period.

In one of the embodiments of the present invention a slot is provided on the outer surface of each of the bodies within the zone of the recess for one end of the spacer to pass into, while the other end of the spacer is made fast on the free end of the jaw, and a movable knife is held to the outer surface of each of the bodies, said knife being adapted for cutting off the portion of the spacer which is accommodated in the slot on terminating the operation so as to release the spacers from the instrument jaws.

It is expedient that each of the spacers be made as a flat strip of a springy elastic material as wide as the instrument jaw, and that a strap is provided at one of the ends of the strip integral therewith, said strap being adapted to be accommodated in the slot, while the end of the strip is shaped as a cup-like member adapted to be fitted onto the free end of the jaw.

BRIEF DESCRIPTION OF THE DRAWINGS

Given below is a detailed description of a specific embodiment of the present invention with reference to the accompanying drawings, wherein:

FIG. 1 is a front elevation view partly cutaway, of an instrument for suturing hollow organs, according to the present invention;

FIG. 2 is a side elevation view of the instrument illustrated in FIG. 1;

DETAILED DESCRIPTION OF THE INVENTION

Figure 3:
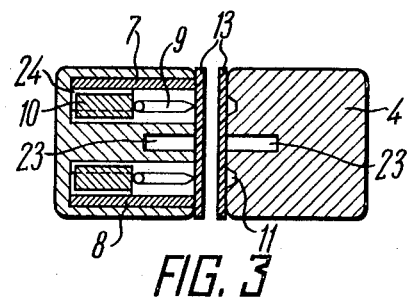
FIG. 3 is a section taken on the line III—III in FIG. 1.
Figure 4:
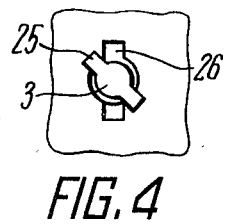
FIG. 4 is a view facing the arrow B in FIG. 2.
Figure 5:
FIG. 5 is a section taken on the line V—V in FIG. 1.

Reference being now directed to FIGS. 1, 2 and 3, the herein-disclosed instrument for suturing hollow organs adapted, according to the present invention, to establish a lateral compression anastomosis is shown to comprise respective supporting and staple bodies 1 and 2, hinge-joined to each other through a pin 3 (FIGS. 1 and 2). The bodies have respective longitudinal jaws 4 and 5 provided at one of their ends and are provided with finger-receiving rings 6 at their other ends. The longitudinal jaw 5 of the staple body 2 carries replaceable staple magazines 7 and 8 (FIGS. 1, 3) along with staples 9 and ejectors 10 of the staples 9. The longitudinal jaw 4 of the supporting body 1 has a die or anvil 11 for bending the staples 9. A shaped recess 12 is formed at the proximal end of the jaws 4 and 5 at the base thereof, i.e., at the bottom region thereof proximate to the hinge joint, defining a free space between the jaws 4 and 5 when they are brought into contiguous relationship during a suturing procedure. The longitudinal jaws 4 and 5 carry springy elastic spacers 13 having cup-shaped endpieces 14 and straps 15 for securing the spacers 13 to the jaws 4 and 5. Slots 16 are provided in the bodies 1 and 2 at the base of the jaws 4 and 5, said slots being adapted to accommodate the straps 15 provided at the ends of the spacers 13 and to mount knives 17 and 18, the straps 15 of the spacers 13 being arranged in the slots 16 before the knives 17 and 18. A slider 19 is provided on the staple body 2 to which a plate knife 21 and wedge-shaped ejectors 22 are held by screws 2 for feeding the staples 9 out of the magazines 7 and 8. The ejectors 22 are traversable in slits 23 and 24 (FIGS. 1 and 3). The slit 23 accommodating the knife 21 has a variable shape so as to make it possible to cut through the spacers 13 and the tissues being sutured beyond the reces 12. Projections 25 ar reprovided at the end of the pin 3 adapted to enter slots 26 (FIG. 4) in the supporting body 1 so as to form a separable single-lug lock. When brought together the supporting and staple bodies are locked by a locking pawl 27 (FIG. 5).

The surgical instrument for sturing hollow organs, according to the present invention, operates as follows.

Figure 6:
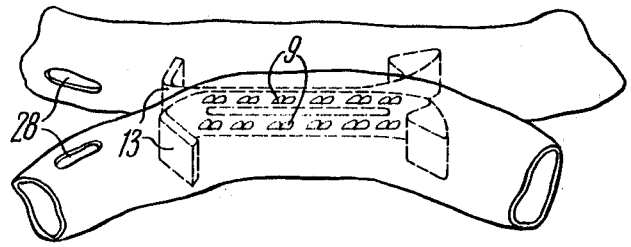
FIG. 6 is a lateral compression anastomosis established with the use of the instrument of FIG. 1.

In order to establish, for example, a lateral gastrointestinal compression anastomoses, the supporting body 1 and the staple body 2 are set apart and the longitudinal jaws 4 and 5 are completely introduced into the interior of the organs being sutured through punctures 28 (FIG. 6). Then the supporting body 1 and the staple body 2 of the instrument are brought together and locked to each other with the rings 6 by drawing them together until locked with the pawl 27. Next the slider 19 along with the plate knife 21 and the wedge ejectors 22 is moved along the staple body of the instrument towards the longitudinal jaws 4 and 5 till meeting a stop. As a result nearly simultaneous suturing of the elastic spacers 13 and the walls of the organs involved are sutured and intersected to establish communication between the gastric stump and the enteric loop. Thereupon the knives 17 and 18 are advanced to intersect the straps 15 of the spacers 13, whereupon the slider 19 is returned to the initial position. The longitudinal jaws 4 and 5 are moved apart and withdrawn from the interior spaces of the thus-sutured organs having been already stripped of the elastic spacers 13. Further manipulations aimed at stitching up the punctures are carried out manually according to the heretofore adopted commonly known techniques.

As a result of the operation performed with the use of the instrument disclosed in the present invention a compression anastomosis is established, isolated from the punctures in the walls of the organs sutured. Thus, these organ walls in the zone of the punctures can be stitched up manually, and are not subjected whatever to compression by the instrument jaws, which contributes to better healing of the walls. In a certain period of time (7 to 10 days) the thus-sutured organs reunite along the perimeter of the compression anastomosis established, while the spacers 13 along with the staples 9 are rejected and removed from the organism by natural way. Thus, a high-quality "sutureless" anastomosis is obtained conducive to good physiological functions of the organs involved.

To stitch up the mesentery along great lengths thereof upon excision of morbidly changed intestine segments, the instrument is not set apart into two halves, but is used as a clamp. A puncture is made in the mesentery with the pointed end of one of the jaws, say the jaw 5, whereupon that jaw is introduced for the full length thereof into the mesentery. Then the jaws 4 and 5 of the respective bodies 1 and 2 are brought together and locked with the pawl 27, with the result that the mesentery gets uniformly compresseed between the jaws 4 and 5 fitted with the springy elastic spacers 13 to provide good hermetic tightness. Then the mesentery is sutured by the instrument and simultaneously severed along the thus-applied suture. Next the jaws 4 and 5 are set apart, instrument is withdrawn, the fresh magazines 7 and 8 and the spacers 13 are charged into the instrument, and a next length of the mesentery is stitched up in a similar way. Stitching up the mesentery with the use of the herein-disclosed instrument employing springy elastic spacers provides for a reliable hemostasis, while an adequate length of the instrument jaws ensures good productivity of suturing, which enables the operating time to be cut down several fold.

The herein-disclosed surgical instrument for suturing hollow organs is simple in construction and application techniques, convenient to handle and is easy-to-master by the surgeon. In addition, the instrument provides for establishing high-quality lateral compression anastomoses and quick stitching up of the mesentery over great lengths thereof to obtain a good hemostasis.

While a preferred embodiment of the present invention has been disclosed in the foregoing description, it will be understood that various modifications and versions may occur to those skilled in the art without departing from the spirit and scope of the invention, as defined in the Claims that follow.

What we claim is:

1. In a surgical instrument for staple suturing hollow organs including a staple body and a supporting body hingedly connected thereto at a hinge joint, said bodies having outer surfaces and longitudinally extending jaws having respective compressing inner side surfaces adpated to be brought to mutual contiguous relationship with each other during a suturing procedure, said staple body having a staple magazine and ejector means for feeding the staples from said magazine during a suturing procedure in the region of the staple body jaw, said supporting body having die means for bending the staples fed from the magazine during the suturing procedure in the region of the supporting body jaw; the improvement comprising:

at least one of said staple and supporting bodies are formed to define a recess between said bodies in a bottom region of said side surface of at least one of said jaws proximate to said hinge joint, said recess defining an enlarged free space between said jaws when the same are in mutual contiguous relationship with each other during a suturing procedure and so that compression will not be applied to the regions of the organs to be sutured which are situated within said free space during a suturing procedure; a pair of spacers formed of springy elastic material adapted to be mounted and secured to respective jaws over the respective compression side surfaces thereof so as to be stitched up together with the organs to be sutured during a suturing procedure; and means for releasing said spacers from said respective jaws after termination of the suturing procedure.

2. In a surgical instrument for staple suturing hollow organs including a staple body and a supporting body hingedly connected thereto at a hinge joint, said bodies having outer surfaces and longitudinally extending jaws having respective compressing inner side surfaces adapted to be brought to mutual contiguous relationship with each other during a suturing procedure, said staple body having a staple magazine and ejector means for feeding the staples from said magazine during a suturing procedure in the region of the staple body jaw, said supporting body having die means for bending the staples fed from the magazine during the suturing procedure in the region of the supporting body jaw; the improvement comprising:

at least one of said staple and supporting bodies are formed to define a recess between said bodies in a bottom region of said side surface of at least one of said jaws proximate to said hinge joint, said recess defining a free space between said jaws when the same are in mutual contiguous relationship with each other during a suturing procedure; a pair of spacers formed of springy elastic material adapted to be mounted and secured to respective jaws over the respective compressing side surfaces thereof so as to be stitched up together with the organs to be sutured during a suturing procedure; and means for releasing said spacers from said respective jaws after termination of the suturing procedure; and wherein each spacer is constituted by an elongate member having two ends and wherein a slot is formed on an outer surface of each of said staple and supporting bodies in the region of said recess, one end of each spacer being received in a respective one of said slots and wherein the other end of each spacer is secured to a free end of a respective jaw, and wherein said spacer releasing means include a knife member movably mounted to an outer surface of each of said staple and supporting bodies adapted to move between a retracted position and a position wherein it severs that portion of a spacer which is received in the respective slot on termination of the suturing procedure so as to release the spacers from the jaws.

3. The combination of claim 2 wherein each of said spacers comprises a flat strip portion formed of springy elastic material having substantially the same width as the respective jaw to which it is secured, a strap portion integrally formed on one end of said flat strip portion adapted to be received in a repective one of said slots, and a cup-shaped portion integrally formed on the other end of said flat strip portion adapted to be fitted over the free end of the respective jaw to which the spacer is secured.

* * * * *